United States Patent
Chou

(10) Patent No.: US 10,588,580 B2
(45) Date of Patent: Mar. 17, 2020

(54) TOUCH-CONTROLLED ASSEMBLY

(71) Applicant: CAL-COMP BIG DATA, INC., New Taipei (TW)

(72) Inventor: Yi-Wen Chou, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 18 days.

(21) Appl. No.: 15/613,143

(22) Filed: Jun. 3, 2017

(65) Prior Publication Data

US 2018/0279969 A1 Oct. 4, 2018

(30) Foreign Application Priority Data

Mar. 31, 2017 (CN) .......................... 2017 1 0205712

(51) Int. Cl.
  *G06F 3/044* (2006.01)
  *A61B 5/00* (2006.01)
  *H03K 17/96* (2006.01)

(52) U.S. Cl.
  CPC .......... *A61B 5/7475* (2013.01); *A61B 5/0077* (2013.01); *A61B 5/441* (2013.01); *H03K 17/9622* (2013.01); *H03K 2217/96031* (2013.01); *H03K 2217/96077* (2013.01)

(58) Field of Classification Search
  CPC ...... G06F 1/1632; G06F 1/1607; G06F 3/044; G06F 3/04; A61B 5/7475; A61B 5/0077; A61B 5/441; H03K 17/9622; H03K 2217/96031; H03K 2217/96077
  See application file for complete search history.

(56) References Cited

U.S. PATENT DOCUMENTS

| | | | | |
|---|---|---|---|---|
| 2006/0256090 A1* | 11/2006 | Huppi | ..................... | A63F 13/02 345/173 |
| 2013/0240339 A1* | 9/2013 | Miyazaki | .............. | G06F 3/0202 200/5 A |
| 2015/0331451 A1* | 11/2015 | Shin | ....................... | G06F 3/041 345/173 |
| 2015/0334859 A1* | 11/2015 | Lee | ...................... | H05K 5/0247 361/749 |
| 2016/0165027 A1* | 6/2016 | Hahn | ....................... | H04B 1/38 455/566 |
| 2017/0115766 A1* | 4/2017 | Saukko | ................... | G06F 3/044 |
| 2017/0205927 A1* | 7/2017 | Lee | ...................... | H01L 27/323 |

* cited by examiner

*Primary Examiner* — Lunyi Lao
*Assistant Examiner* — Jarurat Suteerawongsa
(74) *Attorney, Agent, or Firm* — JCIPRNET

(57) ABSTRACT

A touch-controlled assembly adapted to an electronic device is provided. The electronic device has a front casing, a rear casing and a display surface, where the display surface is located on the front casing. The touch-controlled assembly includes a circuit board and at least one touch key. The circuit board is disposed between the front casing and the rear casing. The circuit board has at least one pad, which contacts one surface of the rear casing. The at least one touch key is disposed on another surface of the rear casing for corresponding to the at least one pad, where an orthogonal projection of the at least one touch key on the at least on pad is partially overlapped with the at least one pad.

7 Claims, 5 Drawing Sheets

TOUCH-CONTROLLED ASSEMBLY

CROSS-REFERENCE TO RELATED APPLICATION

This application claims the priority benefit of China application serial no. 201710205712.0, filed on Mar. 31, 2017. The entirety of the above-mentioned patent application is hereby incorporated by reference herein and made a part of this specification.

BACKGROUND

Technical Field

The disclosure relates to a touch-controlled assembly.

Description of Related Art

The love of beauty is human nature, and regardless it is from the point of view of beauty or health, everyone wants to have a beautiful appearance. Facial skin condition is an important indicator to determine a person's beautiful degree, so that detection of the facial skin condition becomes very important. In a field of medical cosmetology, the detection of skin condition can only be implemented through naked eye observation of traditional professional medical staff, and the skin condition is analyzed via a subjective experience of the medical staff, so that whether it can meet the actual situation is still under a test.

An existing professional skin detector is used to scan skin to learn the skin condition. Vendor sales staff may also recommend an appropriate skin care product according to the skin condition to promote product sales. However, a user is hard to own a skin detector by himself, and a reason thereof is that the price of the skin detector is very high, and a volume thereof is very large, and the skin detector is installed with a microscope with a different magnification to scan the skin, so that only a small portion of a skin area is scanned in one action, and an operation time of the skin detector is rather long. Moreover, professional training is required to learn how to identify the skin condition through the skin detector. Therefore, for the user who wants to always learn whether his own skin condition is improved, the skin detector is hard to meet the user's actual demand.

On the other hand, an existing consumable electronic device may determine to execute a corresponding function when a finger presses a touch key thereon. However, when the touch key is combined with the aforementioned skin detector, since most of the area facing to the user is occupied by a display device, the touch key is generally configured on a back surface of the device, and a user has to operate through a blind pressing manner, which decreases operation convenience of the electronic device.

Therefore, how to provide a simple operation structure to facilitate the user to easily and conveniently perform the skin detection, record a skin care process, and share the skin care information is important in improvement of the skin detector.

SUMMARY

The disclosure is directed to a touch-controlled assembly, which improves user's operation convenience through a simple component design.

The disclosure provides a touch-controlled assembly adapted to an electronic device. The electronic device has a front casing, a rear casing and a display surface, where the display surface is located on the front casing. The touch-controlled assembly includes a circuit board and at least one touch key. The circuit board is disposed between the front casing and the rear casing. The circuit board has at least one pad, which contacts one surface of the rear casing. The at least one touch key is disposed on another surface of the rear casing for corresponding to the at least one pad, where an orthogonal projection of the at least one touch key on the at least on pad is partially overlapped with the at least one pad.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF EMBODIMENTS

Figure 1:
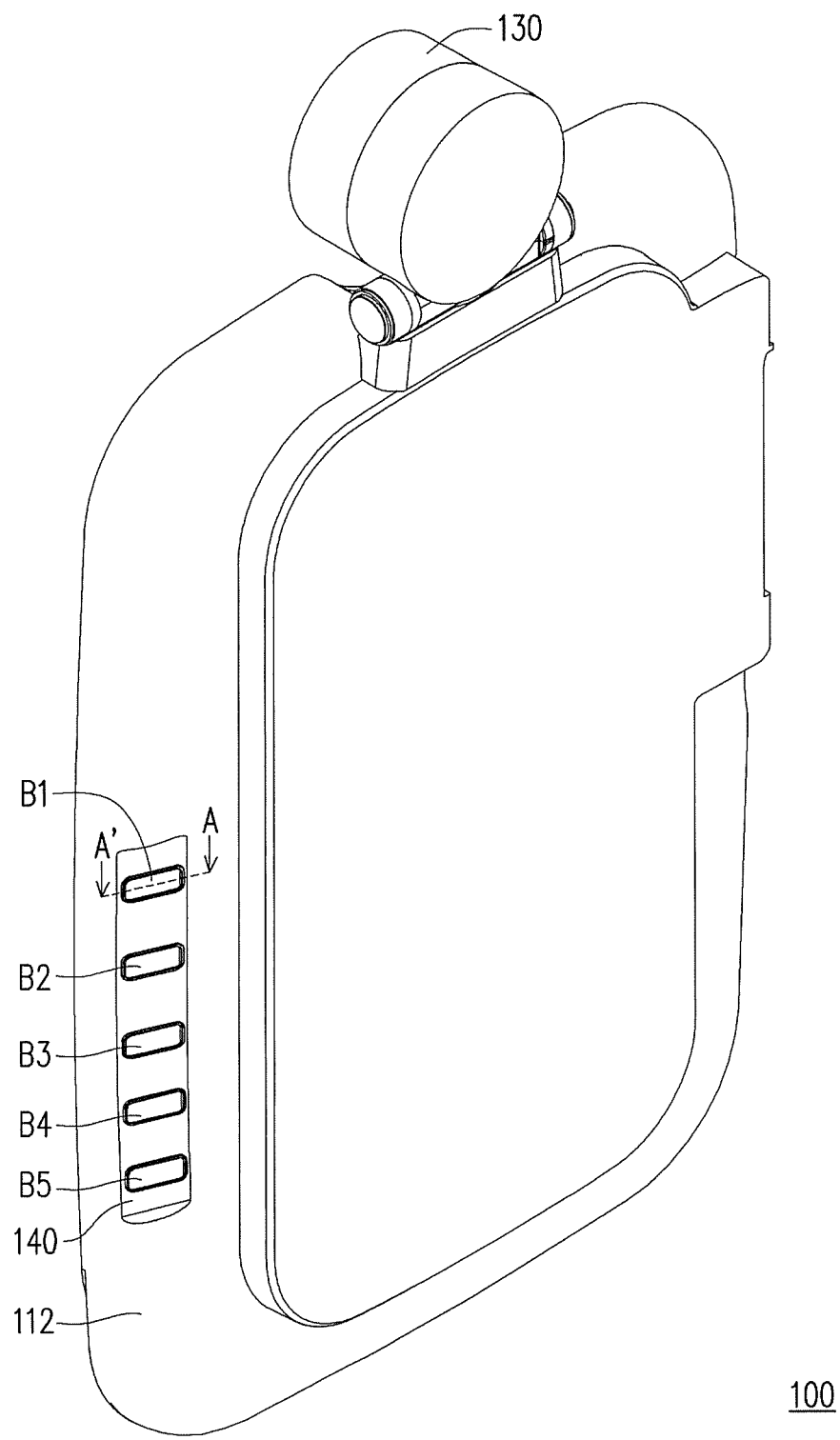
FIG. 1 is a schematic diagram of an electronic device according to an embodiment of the disclosure.

Reference will now be made in detail to the present preferred embodiments of the disclosure, examples of which are illustrated in the accompanying drawings. Wherever possible, the same reference numbers are used in the drawings and the description to refer to the same or like parts.

Figure 2:
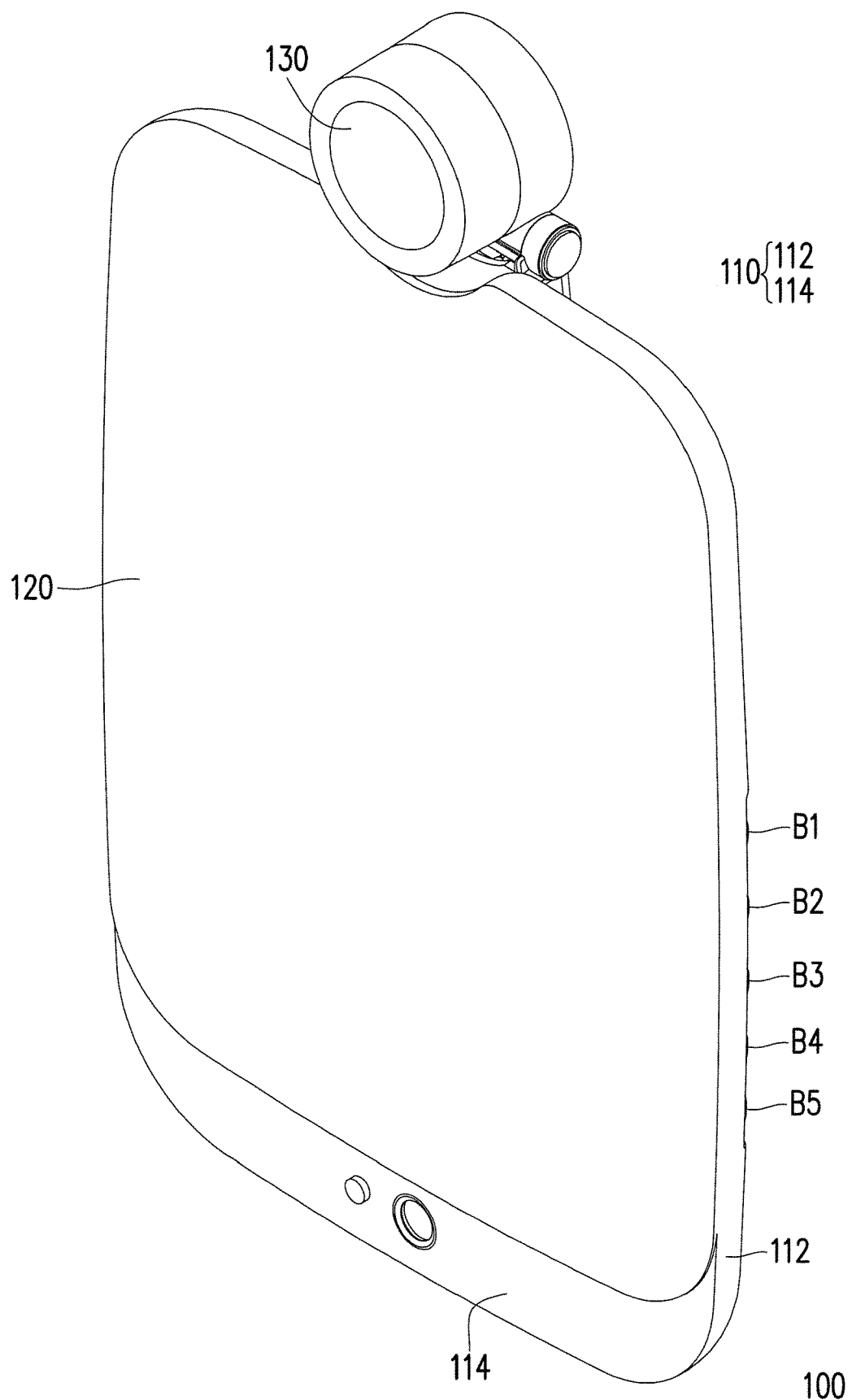
FIG. 2 is a schematic diagram of the electronic device of FIG. 1 viewing in another viewing angle.

FIG. 1 is a schematic diagram of an electronic device according to an embodiment of the disclosure. FIG. 2 is a schematic diagram of the electronic device of FIG. 1 viewing in another viewing angle. In the present embodiment, the electronic device 100 is, for example, a smart mirror, which includes a main body 110, a display device 120 and an image capturing device 130, where the main body 110 is formed by assembling a front casing 114 and a rear casing 112, the display device 120 is, for example, a liquid crystal display (LCD), which is disposed on the front casing 114 to form a display surface. The image capturing device 130 is disposed on the top of the main body 110, and a user is adapted to be located in front of the display surface, and user's face is captured by the image capturing device 130, so as to detect skin condition information of the user's face, and a face image of the user and the skin condition information are displayed on the display surface of the display device 120 to facilitate the user learning the skin condition of himself. The skin condition information includes variation features of wrinkles, facial lines, erythema, acne, spots, pores, a skin color, a dark circle, etc., and a processor (not shown) of the electronic device 100 obtains the variation features according to a specific determination reference and severity thereof, and calculates a plurality of skin parameters, for example, clearness, texture, firmness, brightness, healthiness, etc. according to the variation features, though the disclosure is not limited thereto.

Figure 3:
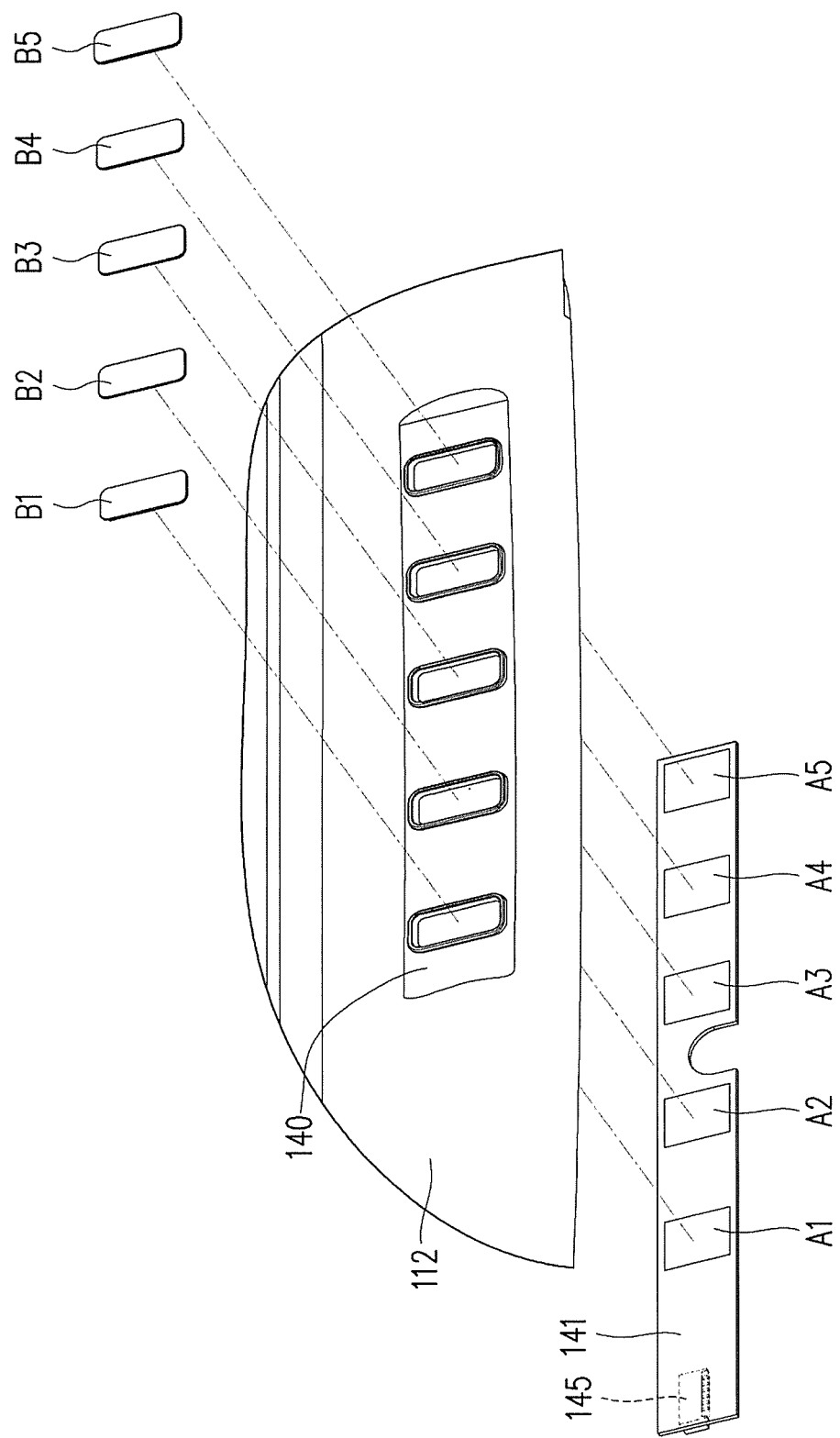
FIG. 3 is a schematic diagram of assembling a part of components of the electronic device of FIG. 1.
Figure 4:
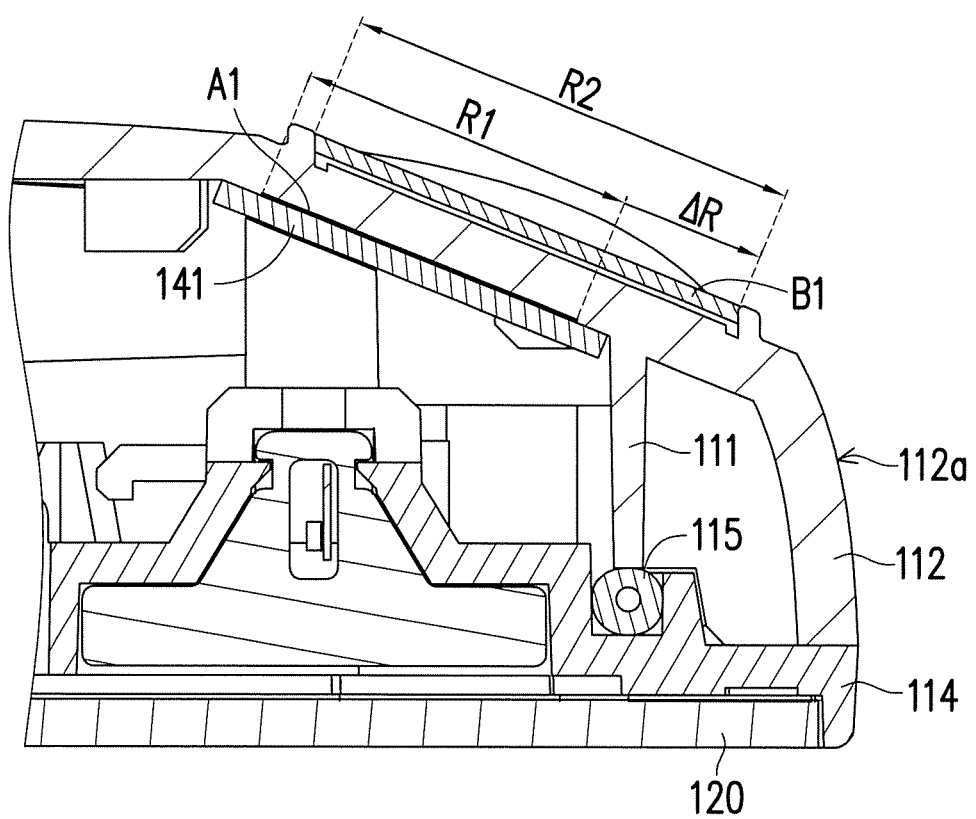
FIG. 4 is a cross-sectional view of the electronic device of FIG. 1 viewing along a section line A-A'.
Figure 5:
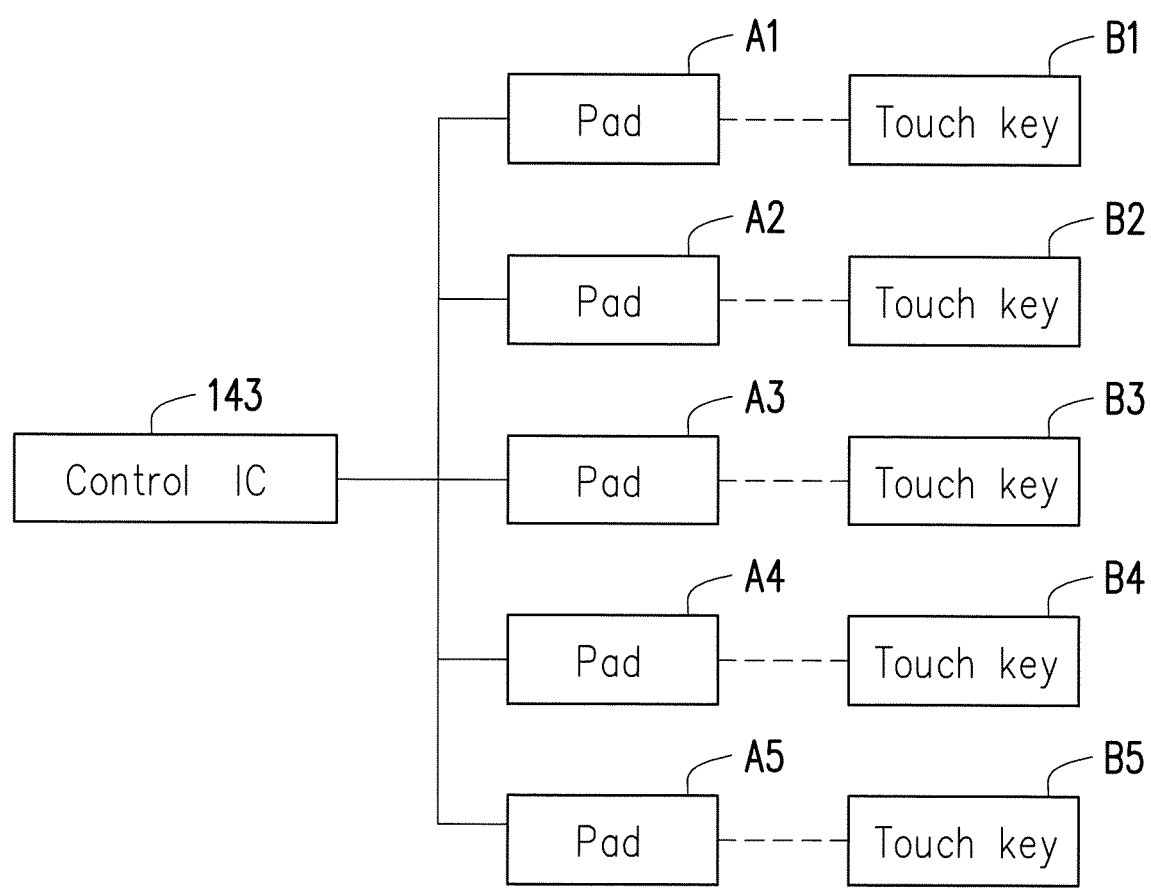
FIG. 5 illustrates an electrical connection relationship of a touch-controlled assembly.

FIG. 3 is a schematic diagram of assembling a part of components of the electronic device of FIG. 1. FIG. 4 is a cross-sectional view of the electronic device of FIG. 1 viewing along a section line A-A'. FIG. 5 illustrates an electrical connection relationship of a touch-controlled assembly. Referring to FIG. 3 to FIG. 5, in the present embodiment, the electronic device 100 further includes a touch-controlled assembly 140, which is disposed in the main body 110, and the touch-controlled assembly 140 includes a circuit board 141 and at least one touch key, where the touch keys are disposed in grooves of the rear casing 112, as that shown in FIG. 3, the circuit board 141 is disposed between the front casing 114 and the rear casing 112, and the circuit board 141 has at least one pad. The at least one pad includes 5 pads A1-A5, though the disclosure is not limited thereto, and the at least one touch key includes 5 touch keys B1-B5, though the disclosure is not limited thereto. The pads A1-A5 are, for example, adhered to an inner surface of the rear casing 112 through a conductive adhesive, and the touch keys B1-B5 are, for example, adhered to an outer surface of the rear casing 112 through the conductive adhesive, such that the pads A1-A5 and the touch keys B1-B5 are aligned with each other, where the touch keys B1-B5 have conductivity (a material thereof is, for example, metal, for electrical connection). Meanwhile, as shown in FIG. 5, the circuit board 141 is further packaged with a control IC 143, which is respectively and electrically connected to the pads A1-A5, and the circuit board 141 is electrically connected to the processor of the electronic device 100 through a connector interface 145. The type of the circuit board 141 of the present embodiment is not limited, and in another embodiment that is not shown, a flexible circuit board can also be used.

In this way, as shown in FIG. 4, the rear casing 112 is closely attached between the pads A1-A5 and the touch keys B1-B5 in structure without a gap there between, such that the pads A1-A5 and the touch keys B1-B5 form capacitor structures. The so-called "without a gap there between" indicates that only the rear casing 112 is located between the pads A1-A5 and the touch keys B1-B5 without other medium including air. As shown in FIG. 1 and FIG. 5, the user may change capacitances between the pads A1-A5 and the touch keys B1-B5 by touch the touch keys B1-B5, so as to achieve an effect of triggering the control IC 143. Namely, the touch-controlled assembly 140 of the present embodiment is a capacitive touch input assembly, and the user may touch the touch keys B1-B5 to trigger the electronic device 100 to execute specific functions.

It should be noted that as shown in FIG. 1 and FIG. 2, since the user is located in front of the display surface, in order to ensure the user to smoothly touch the touch keys B1-B5, in the present embodiment, as shown in FIG. 4, an orthogonal projection of the touch key B1 on the pad A1 is partially overlapped with the pad A1, and meanwhile the touch key B1 extends from the place corresponding to the pad A1 towards an outer edge 112a of the rear casing 112, and as the outer edge 112a presents an arc profile, the user may easily view the touch key B1 for touching, and other touch keys B2-B5 have the same configuration.

Further, as shown in FIG. 4, the rear casing 112 of the present embodiment further has a rib 111, which extends towards the front casing 114. The electronic device 100 further includes a sealing member 115, which is disposed in a recess of the front casing 114 and is leaned against by the rib 111, so as to achieve an effect of sealing an internal space of the main body 110 of the electronic device 100, and provide a protection function (waterproof, dust proof) for the electronic components (for example, the circuit board 141 of the touch-controlled assembly 140) set in the main body 110.

Limited by the aforementioned protection mechanism, a position where the the circuit board 141 of the touch-controlled assembly 140 is closest to the outer edge 112a is an inner side of the rib 111 located adjacent to the circuit board 141 (i.e. a left side of the rib 111 in FIG. 4), such that the circuit board 141 substantially leans against a base portion of the rib 111 (the base portion is opposite to a tail end of the rib 111 that leans against the sealing member 115). Under such circumstances, the touch keys B1-B5 are required to stride over from a corresponding place of the inner side of the rib 111 to a corresponding place of the outer side of the rib 111 to achieve the effect of extending the aforementioned capacitor structure. Namely, through the component configuration of FIG. 4, an orthogonal projection of the base portion of the rib 111 on the touch key B1 is located within a range of the touch key B1.

In detail, as shown in FIG. 4, the pad A1 has a fixed touch region R1, though limited by the aforementioned rib 111, the portion of the pad A1 corresponding to the rear casing 112 is not easy for the user to touch. Therefore, a touch region R2 formed by the touch key B1 further has an extending region AR extending towards the outer edge 112a compared to the touch region R1, so that the position where the extending region AR is located can be smoothly touched by the user. Meanwhile, in order to make the pads A1-A5 and the touch keys B1-B5 to maintain a minimum induction capacitance difference required for triggering the control IC 143, under a premise that the pads A1-A5 respectively have a size of 14 mm×12 mm, an overlapped area between the orthogonal projection of the touch keys B1-B5 on the circuit board 141 and the pads A1-A5 is greater than or equal to 40% of an area of the pads A1-A5.

In summary, in the touch-controlled assembly of the aforementioned embodiment, the capacitor structures are formed through the touch keys and the pads, and in structural configuration, the touch keys and the pads corresponding to each other are partially overlapped, so that the touchable regions of the touch keys further have the extending regions extending towards the outer edge of the main body compared to the touch regions of the pads. Therefore, when the user is located in front of the display surface of the electronic device, the user may still easily touch the touch keys on the rear casing, so as to achieve the effects of triggering and executing the specific functions of the electronic device, and improve usage convenience.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A touch-controlled assembly, adapted to an electronic device, the electronic device having a front casing, a rear casing and a display surface, wherein the display surface is located on the front casing, the touch-controlled assembly comprising:
 a circuit board, disposed between the front casing and the rear casing, and having at least one pad, wherein the at least one pad contacts one surface of the rear casing; and at least one touch key, disposed on another surface of the rear casing for corresponding to the at least one pad, wherein the rear casing is located between the at least one pad and the at least one touch key without a gap and without other medium therebetween, an orthogonal projection of the at least one touch key on the at least one pad is only partially overlapped with the at least one pad, the at least one touch key extends further than the at least one pad in a first direction towards an outer edge of the rear casing, the at least one pad extends further than the at least one touch key in a second direction opposite to the first direction, the orthogonal projection of the at least one touch key on the at least one pad that is not overlapped with the at least one pad is an extending region of a touch region of the touch key extending towards the outer edge of the rear casing, so that the extending region can be smoothly touched, wherein the rear casing has a rib that overlaps the extending region, and wherein an overlapped area between an orthogonal projection area of the at least one touch key on the circuit board and an area of the at least one pad is greater than or equal to 40% of the area of the at least one pad.

2. The touch-controlled assembly as claimed in claim 1, wherein the touch-controlled assembly is a capacitive touch input assembly.

3. The touch-controlled assembly as claimed in claim 1, wherein the at least one touch key is conductive.

4. The touch-controlled assembly as claimed in claim 1, wherein the rib extends towards the front casing, the circuit board is located adjacent to an inner side of the rib, and the at least one touch key strides over from a corresponding place of the inner side of the rib to a corresponding place of an outer side of the rib.

5. The touch-controlled assembly as claimed in claim 4, wherein an orthogonal projection of a base portion of the rib on the at least one touch key is located within a range of the at least one touch key.

6. The touch-controlled assembly as claimed in claim 4, further comprising:
   a sealing member, disposed in a recess of the front casing and leaned against by the rib.

7. The touch-controlled assembly as claimed in claim 1, wherein the circuit board is a flexible circuit board.

* * * * *